United States Patent
Yamane et al.

(10) Patent No.: US 8,699,783 B2
(45) Date of Patent: Apr. 15, 2014

(54) MASK DEFECT INSPECTION METHOD AND DEFECT INSPECTION APPARATUS

(75) Inventors: Takeshi Yamane, Tsukuba (JP); Tsuneo Terasawa, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 269 days.

(21) Appl. No.: 13/230,030

(22) Filed: Sep. 12, 2011

(65) Prior Publication Data

US 2012/0063667 A1    Mar. 15, 2012

(30) Foreign Application Priority Data

Sep. 13, 2010 (JP) .................................. 2010-204743

(51) Int. Cl.
*G06K 9/00* (2006.01)
(52) U.S. Cl.
USPC ......................................... 382/144; 382/149
(58) Field of Classification Search
USPC .................................................. 382/144, 149
See application file for complete search history.

(56) References Cited

U.S. PATENT DOCUMENTS

| | | | |
|---|---|---|---|
| 6,954,266 B2 | 10/2005 | Tomie | |
| 7,005,649 B1 | 2/2006 | Tezuka et al. | |
| 7,630,068 B2 * | 12/2009 | Tanaka et al. | 356/237.1 |
| 7,911,600 B2 * | 3/2011 | Terasawa et al. | 356/237.5 |

FOREIGN PATENT DOCUMENTS

| | | |
|---|---|---|
| JP | 3068636 | 5/2000 |
| JP | 3728495 | 10/2005 |

OTHER PUBLICATIONS

Takeshi Yamane ; Toshihiko Tanaka ; Tsuneo Terasawa and Osamu Suga "Actinic EUVL mask blank inspection capability with time delay integration mode", Proc. SPIE 7748, Photomask and Next-Generation Lithography Mask Technology XVII, 774803 (May 26, 2010).*

Yoshihiro Tezuka ; Masaaki Ito ; Tsuneo Terasawa and Toshihisa Tomie "Actinic detection and screening of multilayer defects on EUV mask blanks using dark-field imaging", Proc. SPIE 5446, Photomask and Next-Generation Lithography Mask Technology XI, 870 (Aug. 20, 2004).*

* cited by examiner

*Primary Examiner* — Utpal Shah
(74) *Attorney, Agent, or Firm* — Finnegan, Henderson, Farabow, Garrett & Dunner, LLP

(57) ABSTRACT

According to one embodiment, in a method for inspecting a defect of an exposure mask, using an optical system which acquires a dark-field image, an arbitrary partial region where a uniform dark-field image is obtained on the mask is allocated at a defocus position to acquire an image. A detection threshold is decided using signal intensities of the acquired image and an area ratio between a desired inspection region and the partial region, so that a signal count indicating signal intensities greater than the detection threshold in the inspection region is less than a target false detection count. The mask is allocated in a just-in-focus position to acquire an image of the inspection region. A signal having a signal intensity of the acquired image, which indicates an intensity greater than the detection threshold, is determined as a defect.

16 Claims, 4 Drawing Sheets

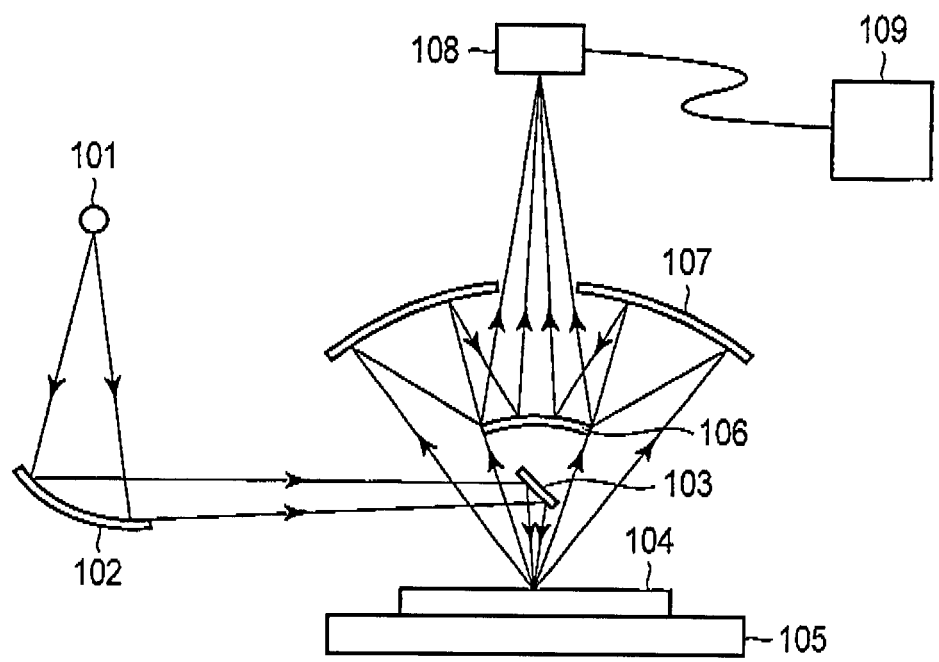
F I G. 1

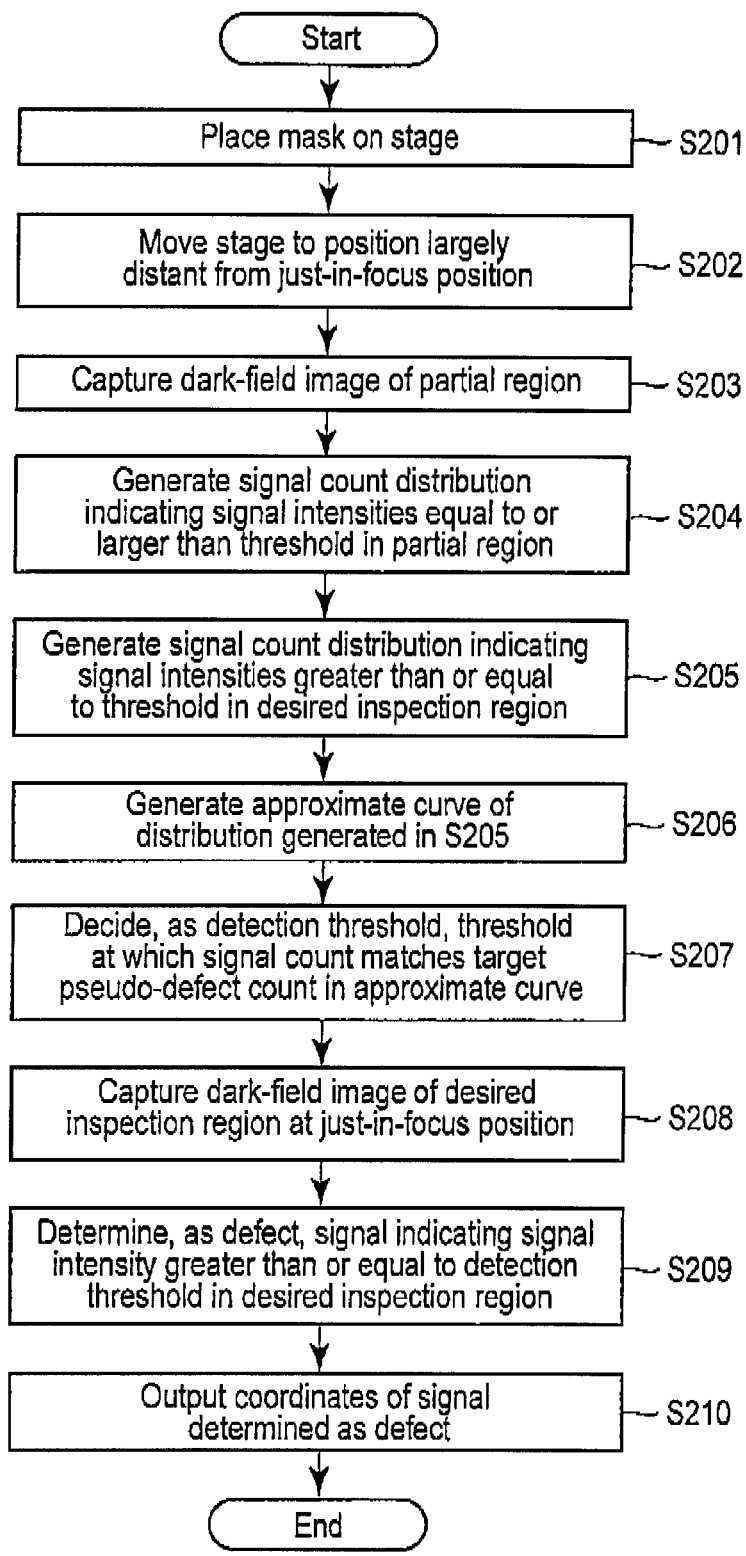
F I G. 2

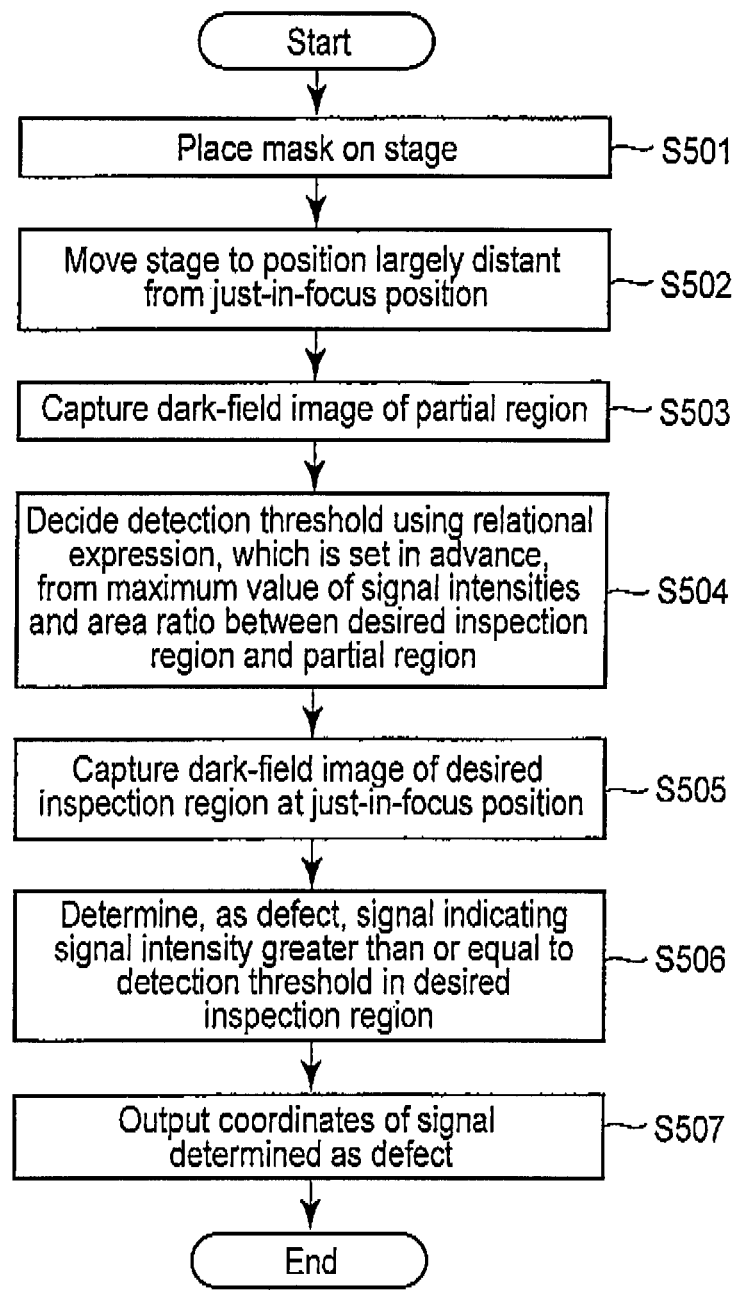
F I G. 5

MASK DEFECT INSPECTION METHOD AND DEFECT INSPECTION APPARATUS

CROSS-REFERENCE TO RELATED APPLICATIONS

This application is based upon and claims the benefit of priority from prior Japanese Patent Application No. 2010-204743, filed Sep. 13, 2010, the entire contents of which are incorporated herein by reference.

FIELD

Embodiments described herein relate generally to a mask defect inspection method and defect inspection apparatus used in defect inspections of a semiconductor exposure mask.

BACKGROUND

A semiconductor exposure mask is fabricated by forming, by, for example, etching, a desired pattern on a blank mask prepared by depositing a light-shielding film (or reflecting film and an absorption film) on a glass substrate. In this case, when extraneous materials and the like exist on the glass substrate and the respective films or in the films, a light-shielding performance of the light-shielding film or a reflecting performance of a reflecting multi-layered film deteriorates. Furthermore, such materials disturb subsequent development and etching processes, and a formed pattern has an abnormal shape, resulting in risk of a mask performance drop. Therefore, at the time of fabrication of the exposure mask, whether or not extraneous materials, phase defects, and the like exist has to be inspected in a state of the blank mask.

In an exposure mask using extreme-ultraviolet rays, two different layers having different refractive index, which are called a multi-layered film, are alternately stacked as a reflecting film, so as to adjust phases of reflected light from the respective layers, thus increasing a reflectance. For this reason, when there are extraneous materials and scratches on a glass substrate, the multi-layered film formed on that substrate is locally raised or caved. In this case, since a gradient region where the phases of the reflected light are disturbed (phase defects) is generated, this region is unwantedly transferred onto a wafer at the time of exposure. Hence, as a defect inspection method of an exposure blank mask of extreme-ultraviolet rays, a method of detecting a dark-field image, and detecting signals having intensities greater than or equal to a detection threshold, which is set in advance, as defects is promising.

However, in the mask defect inspection method using a dark-field image, when a CCD camera which captures the dark-field image suffers detection noise, the detection noise is observed as a signal similar to a defect signal (false detection). Therefore, when a low detection threshold is set, it becomes easy to detect weak defect signals, but false detections tend to occur. When the false detections have occurred, operations for accessing a detection position again after inspection, and confirming whether or not a detected defect is an actual or false detection are required, thus requiring much labor and time for the inspection process. On the other hand, when a high detection threshold is set, although false detections are not easily generated, weak defect signals cannot be detected, resulting in low detection sensitivity. As a result, defects to be normally detected may be overlooked.

BRIEF DESCRIPTION OF THE DRAWINGS

FIG. 1 is a schematic view showing an example of the arrangement of a dark-field optical system used in the first embodiment;

FIG. 2 is a flowchart for explaining a mask defect inspection method according to the first embodiment;

FIG. 5 is a flowchart for explaining a mask defect inspection method according to the second embodiment.

DETAILED DESCRIPTION

Figure 3A:
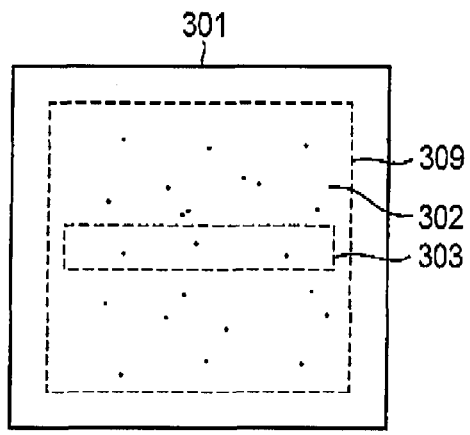
FIGS. 3A, 3B, and 3C are views showing a mask which is to undergo defect inspections, and its dark-field image.

In general, according to one embodiment, in a method for inspecting the presence/absence of a defect of an exposure mask, using an optical system which acquires a dark-field image by irradiating the mask with light of an arbitrary wavelength, an arbitrary partial region where a uniform dark-field image is obtained on the mask is allocated at a defocus position to acquire an image. A detection threshold is decided using signal intensities of the acquired image of the partial region and an area ratio between a desired inspection region and the partial region, so that a signal count indicating signal intensities greater than or equal to the detection threshold in the desired inspection region is less than or equal to a target false detection count. Then, the mask is allocated in the vicinity of a just-in-focus position to acquire an image of the desired inspection region. A signal having a signal intensity of the acquired image of the desired inspection region, which indicates an intensity greater than or equal to the detection threshold, is determined as a defect.

When defects of a blank mask are to be detected by acquiring a dark-field image, it is desirable to set a detection threshold to be slightly higher than a detection noise intensity, so as to obtain a high detection sensitivity without causing any false detections. However, the detection noise intensity changes depending on, for example, the intensity of a light source and the surface roughness of a blank mask as a cause of generation of weak scattering light. Therefore, every time an inspection is performed, it is required to accurately grasp the detection noise intensity and count using a blank mask which is to undergo the inspection, and to set an appropriate detection threshold.

Hence, one embodiment proposes a technique for accurately grasping the detection noise intensity and count, and setting a detection threshold so that the detection noise count becomes less than or equal to a target count. Embodiments will be described hereinafter with reference to the drawing.

First Embodiment

FIG. 1 is a schematic view showing an example of the arrangement of a dark-field optical system used in a mask defect inspection method according to the first embodiment.

Referring to FIG. 1, reference numeral 101 denotes a light source which emits extreme-ultraviolet rays. The light rays emitted by this light source 101 are reflected and converged by an elliptic mirror 102, and are reflected by a planar mirror 103, thus irradiating the surface of a mask 104 with the light rays. The mask 104 is placed on a mask stage 105, which is movable in XYZ directions. Scattering light rays whose radiation angles are less than an arbitrary angle of those scattered by the mask 104 are shielded by a light-shielding portion of a light-shielding portion/convex mirror 106. The scattering light rays which are not shielded by the light-shielding portion are reflected and focused by a concave mirror 107, and form an image on a CCD detector 108 by a convex mirror of the light-shielding portion/convex mirror 106. The CCD detector 108 detects the image on the mask 104 formed by the scattering light rays coming from the mask 104, and this detection signal is input to a personal computer 109. The personal computer 109 calculates a detection threshold from the image intensities obtained by the CCD detector 108, and determines signals which indicate intensities greater than or equal to the detection threshold as defects.

The arrangement itself of the dark-field optical system is not novel but is known, and the system need only acquire a dark-field image by irradiating the mask 104 with light rays of an arbitrary wavelength. Therefore, the arrangements of the respective units can be changed as needed.

A mask defect inspection method according to this embodiment will be described below with reference to the flowchart shown in FIG. 2.

A blank mask 301 (104) shown in FIG. 3A is placed on the mask stage 105 using the dark-field optical system shown in FIG. 1 (step S201). Then, the blank mask 301 is moved to a defocus position largely distant from a just-in-focus position in an optical axis direction by moving the mask stage 105 in the Z direction (step S202). It is preferable to set this moving amount to be a value at which images of defects 302 which exist on the surface of the blank mask 301 are not formed on the CCD detector 108, that is, to be at least five times or more of a value obtained by dividing a wavelength λ by the square of the numerical aperture NA $[>(\lambda/NA^2)\times 5]$. More preferably, the moving amount is set to be about 10 to 20 times of the above value.

Figure 3B:
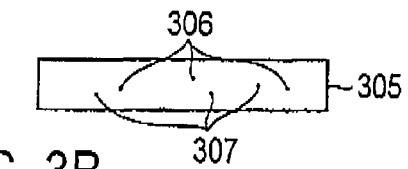
Figure 3C:
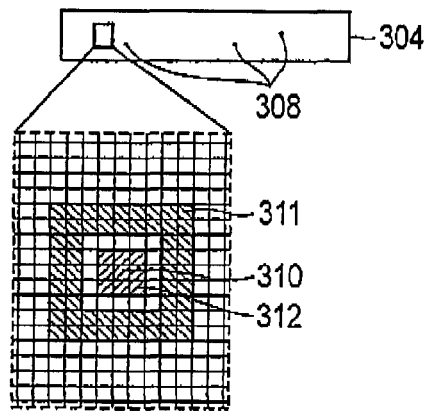

Next, the mask stage 105 is scanned in the X and Y directions to successively acquire a dark-field image of a partial region 303 of the blank mask 301 by the CCD detector 108 using a time delay integration (TDI) method (step S203). FIG. 3C shows an image 304 acquired at this time. On the other hand, FIG. 3B shows an image 305 of the partial region 303 at the just-in-focus position. Note that the image 305 at the just-in-focus position includes noise signals 307 in addition to defect signals 306 corresponding to defects 302, as will be described later, while the image 304 at the defocus position includes only noise signals 308 since no defect signals are imaged. Also, the image 304 is acquired as a set of signal intensities of respective pixels by dividing the partial region 303 by the pixel region of the detector 108.

As described above, the dark-field image of the partial region 303 of the blank mask 301 is captured at the defocus position largely distant from the just-in-focus position. Even if the partial region 303 includes defects, images of the defects do not form any bright spots since the defocus position is largely distant from the just-in-focus position, and bright spots of obtained images are generated by only detection noise components.

Figure 4:
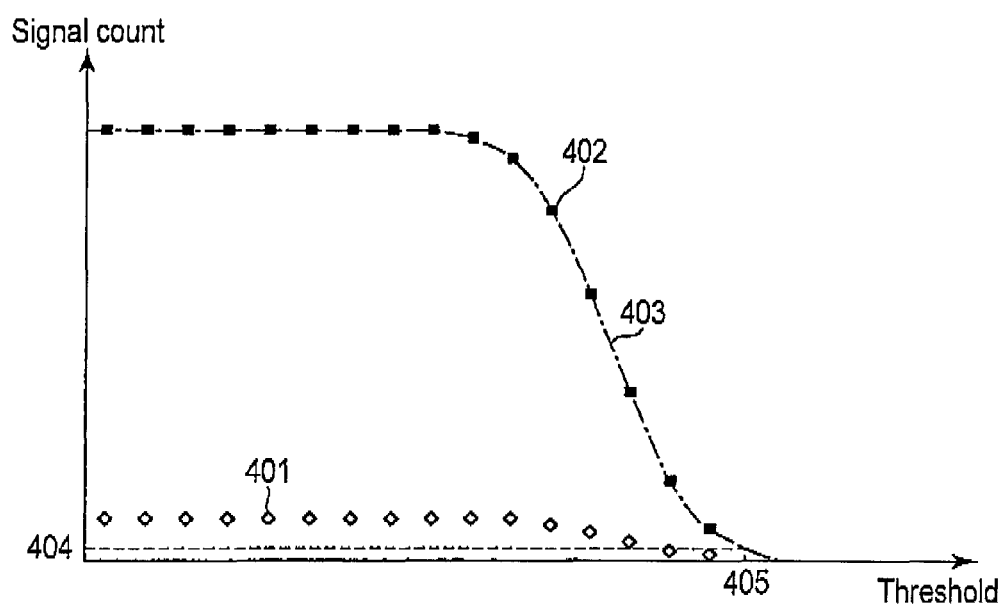
FIG. 4 is a graph showing a signal count distribution in a dark-field image.

By plotting signal counts indicating intensities greater than or equal to a given threshold of signal intensities obtained by acquisition of the dark-field images, as shown in FIG. 4, a distribution 401 of signal counts with respect to the threshold is obtained (step S204). By multiplying the signal count distribution 401 by an area ratio between the partial region 303 and a desired inspection region 309, a signal count distribution 402 in the desired inspection region is obtained (step S205). An approximate curve 403 is generated by fitting-approximating the signal count distribution 402 using an arbitrary function (step S206). In the approximate curve 403, a signal threshold 405 at which a signal count matches an arbitrary target false detection count 404 is calculated and is decided as a detection threshold (step S207). In this case, the target false detection count is an expected value of an allowable false detection count. For example, if one false detection is allowed per 10 inspections, the target false detection count is 0.1.

Next, using the dark-field optical system shown in FIG. 1 again, the blank mask 301 is moved to the just-in-focus position by moving the mask stage 105, so as to acquire an image of the desired inspection region 309 (step S208). When signals included in the obtained image 305 indicate intensities greater than or equal to the detection threshold, these signals are determined as defects (step S209), and coordinates of these signals are recorded (step S210), thus ending the inspection. With this method, the inspection can be performed with the highest defect detection sensitivity while a detection count of the detection noise is suppressed to be an allowable value or lower.

Note that a step of converting signal intensities into peak signal intensities may be inserted between steps S203 and S204 and between steps S208 and S209 in FIG. 2, and the obtained peak signal intensities may be used as signal intensities in steps S204, S205, and S209. In this manner, signal intensity variations due to the influence of illumination light distribution nonuniformity can be eliminated, and signal intensities across a plurality of pixels can be accurately detected. More specifically, letting Iij be a signal intensity of a pixel (i, j) (310 in FIG. 3C), a background B is calculated by calculating an average value of signal intensities of a pixel region (311 in FIG. 3C), which is greater than or equal to a 7×7 pixel region and is less than or equal to a 9×9 pixel region, to have the coordinates (i, j) as the center. Then, a sum total of values obtained by subtracting the background from signal intensities of respective pixels in a pixel region 312 of 3×3 pixels or less, which has the coordinates (i, j) as the center, is defined as a peak intensity Pij, as given by $$P_{ij} = \sum_{n=i-1}^{i+1} \sum_{m=j-1}^{j+1} (I_{nm} - B) \qquad (1)$$

The 3×3 pixel region is decided to be nearly equal to a spread of a defect signal caused by the resolution of an imaging optical system, electron diffusion of the CCD detector, and so forth. The background pixel region (defined by 7×7 to 9×9 pixels) is decided to be sufficiently larger than the spread. At all pixels of a region obtained by excluding a 4-pixel wide outer circumference where a peak signal intensity cannot be calculated of the acquired image, signal intensities Iij are converted into peak signal intensities Pij.

As the area ratio between the partial region 303 and desired inspection region 309 is larger, an acquisition time period required to acquire the image 304 is shorter, while the reliability of the signal count distribution 402 in the desired inspection region is lower. Hence, an actual false detection count is more likely to be different from the target false detection count. Conversely, as the area ratio is smaller, an actual false detection count is more likely to match the target false detection count, while the time period required to acquire the image 304 is prolonged. Therefore, the area ratio has to be adjusted based on the target inspection required time and false detection count.

Note that the processes in steps S204 to S207 are implemented by those of the computer 109. That is, the computer 109 has functions of a first image acquisition unit which acquires an image of the partial region detected by the CCD detector 108 at the defocus position, a threshold decision unit which decides the detection threshold, a second image acquisition unit which acquires an image of the desired inspection region detected by the CCD detector 108 at the just-in-focus position, and a defect determination unit which determines a defect when a signal intensity of the image of the desired inspection region indicates an intensity greater than or equal to the detection threshold.

As described above, according to this embodiment, the dark-field image of the partial region 303 is acquired at the defocus position, and the detection threshold is decided based on the signal intensities of the acquired image, so that a signal count indicating signal intensities greater than or equal to the detection threshold in the desired inspection region 309 becomes less than or equal to the target false detection count. In this manner, the detection threshold that can assure the highest detection sensitivity can be set in a state in which the detection count of detection noise components as defects can be suppressed to an allowable false detection count or less, which is set in advance. Therefore, since the need for identification operations of false detections and actual defects can be obviated, the inspection time and labor can be reduced, and the inspection can be performed with the highest detection performance of the apparatus.

Also, an average value of image intensities in the region 311 outside a region having the position 310 of interest as the center is calculated as the background, and a sum total of values obtained by subtracting the background from image intensities of the region 312 having the position 310 as the center is calculated. Then, the calculated sum total is used as each of the signal intensities of the regions 303 and 309. Thus, signal intensity variations due to the influence of, for example, illumination light distribution nonuniformity can be eliminated.

Note that a technique described in (Japanese Patent No. 3728495) is a most effective method of the techniques for inspecting phase defects of an exposure blank mask using extreme-ultraviolet rays. With this technique, a blank mask is irradiated with extreme-ultraviolet rays to acquire a dark-field image of the blank mask. When there is no defect on the blank mask, only slight scattering light rays caused by the blank mask surface roughness are generated, while when there are defects on the blank mask, since strong scattering light rays are generated from defective portions, defects are observed as bright spots on the dark-field image.

However, it is difficult for this technique to optimally set the detection threshold. When a low detection threshold is set, since a weak defect signal can be detected, a high detection sensitivity can be obtained, while a phenomenon called a false detection, which also erroneously detects the detection noise as a defect, readily occurs. On the other hand, when a high detection threshold is set to suppress a false detection, a weak defect signal cannot be detected, resulting in a low detection sensitivity. Hence, defects to be normally detected may be overlooked. In this embodiment, the detection threshold can be optimally set, as described above, and the inspection can be performed at the highest defect detection sensitivity in a state in which the detection count of the detection noise is suppressed to be equal to or lower than the allowable value.

Also, with a technique described in (Japanese Patent No. 3068636), two objective lenses are used, an image is acquired in a defocus state using one lens to generate reference pattern data free from any defects, an image is acquired in a just-in-focus state using the other lens, and defects are detected by comparing this image with the reference pattern data. Therefore, the arrangement of this technique is quite different from that of this embodiment which detects defects by acquiring a dark-field image.

Second Embodiment

FIG. 5 is a flowchart for explaining a mask defect inspection method according to the second embodiment.

A dark-field optical system used in this embodiment has the same arrangement as that shown in FIG. 1 used in the first embodiment, and a description thereof will not be given. In this embodiment, a difference from the first embodiment is that steps S204 to S207 in FIG. 2 are replaced by step S504 in FIG. 5.

In steps S501 to S503, in a state in which a blank mask 301 is placed on a mask stage 105 and is moved to a defocus position, a dark-field image of a partial region 303 of the blank mask 301 is acquired using a CCD detector 108, as in steps S201 to S203 described above.

In step S504, a relational expression of a maximum value (I) of signal intensities in the partial region 303, a target false detection count (F), an area ratio (R) between a desired inspection region 309 and the partial region 303, and a detection threshold (T) is calculated in advance using the method in steps S204 to S207 described above. This relational expression is calculated using a certain coefficient k by a method which, for example, approximates an empirically obtained value, as given by:

$$T = I + k\log\left(\frac{R}{F}\right) \quad (2)$$

Then, in step S504, a detection threshold is calculated from the area ratio between the desired inspection region 309 and partial region 303 and the maximum value of the signal intensities in the partial region 303 using the above relational expression. Step S505 and subsequent steps are the same as steps S208 and subsequent steps described above. That is, the blank mask 301 is moved to a just-in-focus position to acquire an image of the desired inspection region 309. When a signal of an obtained image 305 indicates an intensity greater than or equal to the detection threshold, this signal is determined as a defect, and the coordinates of the signal are recorded, thus ending the inspection.

As described above, according to this embodiment, since the relational expression of the maximum value (I) of the signal intensities, the target false detection count (F), the area ratio (R), and the detection threshold (T) is calculated in advance, an optimal threshold can be easily set by capturing only the dark-field image of the partial region 303. Therefore, the detection threshold which can assure the highest detection sensitivity without any detection error of the detection noise as a defect can be set by a simpler method than the first embodiment.

(Modification)

Note that the present invention is not limited to the aforementioned embodiments. The first and second embodiments have described the blank mask inspection method. Alternatively, the method of the present invention is applicable to a mask with a pattern. When the partial region described in steps S203, S204, S503, and S504 in FIGS. 2 and 5 above and the desired inspection region described in steps S205, S208, S209, S504, S505, and S506 are replaced by a uniform pattern region such as a region where, for example, line and space patterns are cyclically arranged, the first and second embodiments are applicable to the mask with the pattern.

The arrangement of the dark-field optical system is not limited to FIG. 1 above. The system need only acquire a dark-field image by irradiating a mask with light of an arbitrary wavelength, and can be changed as needed depending on specifications. Furthermore, the defocus amount is not limited to five times or more of the value obtained by dividing the wavelength λ by the square of the numerical aperture NA, but it may be set to be a value that does not resolve defects by a detector such as a CCD. In the above embodiments, the application example to the extreme-ultraviolet ray exposure mask has been described. However, the present invention is applicable to all marks.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A mask defect inspection method comprising:
   configuring an optical system to acquire a dark-field image by irradiating an exposure mask with light having a wavelength, the exposure mask containing a defect;
   positioning the mask at a defocus position spaced away from a just-in-focus position, such that an image of a partial region on the mask at the defocus position contains only a noise signal;
   acquiring, using the optical system, an image of the partial region;
   deciding a detection threshold in a desired inspection region on the mask using signal intensities of the acquired image of the partial region and an area ratio between the desired inspection region and the partial region, so that a signal count indicating signal intensities not less than the detection threshold in the desired inspection region is not more than a target false detection count;
   positioning the mask in a vicinity of the just-in-focus position;
   acquiring an image of the desired inspection region using the optical system; and
   determining, as a defect, a signal having a signal intensity of the acquired image of the desired inspection region, which indicates an intensity not less than the detection threshold.

2. The method according to claim 1, wherein an extreme-ultraviolet ray exposure blank mask is used as the mask.

3. The method according to claim 1, wherein the defocus position is set to be not less than five times of a value obtained by dividing the wavelength of the light by the square of the numerical aperture of the optical system.

4. The method according to claim 1, wherein an average value of image intensities in a region outside a region having a position of interest as a center is calculated as a background, a sum total of values obtained by subtracting the background from image intensities of the region having the position of interest as the center is calculated, and the calculated sum total is used as the signal intensities of the image of the partial region or the desired inspection region.

5. The method according to claim 1, wherein as the optical system, a reflection type illumination optical system which converges light rays emitted from a light source to irradiate the mask with the light rays, and a reflection type imaging optical system which converges and reflects some of scattering light rays from the mask to form an image on a detector are used.

6. The method according to claim 1, wherein in order to decide the threshold, a first signal count distribution for a predetermined threshold is calculated by plotting signal counts indicating intensities not less than the predetermined threshold of signal intensities of the acquired image of the partial region, a second signal count distribution in the desired inspection region is calculated by multiplying the first signal count distribution by an area ratio between the partial area and the desired inspection area, an approximate curve is generated by fitting-approximating the second signal count distribution using an arbitrary function, a signal intensity at which a signal count matches an arbitrary target false detection count is calculated in the generated approximate curve, and the signal intensity is decided as the threshold.

7. A mask defect inspection method comprising:
   configuring an optical system to acquire a dark-field image by irradiating an exposure mask with light having a wavelength, the exposure mask containing a defect;
   positioning the mask at a defocus position spaced away from a just-in-focus position, such that an image of a partial region on the mask at the defocus position contains only a noise signal;
   acquiring, using the optical system, an image of the partial region;
   deciding a detection threshold in a desired inspection region on the mask using an area ratio between the desired inspection region and the partial region, and a maximum value of signal intensities in the partial region, the deciding being performed based on a predetermined relational expression of the maximum value of the signal intensities, a target false detection count, and the area ratio;
   positioning the mask in a vicinity of the just-in-focus position;
   acquiring an image of the desired inspection region using the optical system; and
   determining, as a defect, a signal having a signal intensity of the acquired image of the desired inspection region, which indicates an intensity not less than the detection threshold.

8. The method according to claim 7, wherein an extreme-ultraviolet ray exposure blank mask is used as the mask.

9. The method according to claim 7, wherein the defocus position is set to be not less than five times of a value obtained by dividing the wavelength of the light by the square of the numerical aperture of the optical system.

10. The method according to claim 7, wherein as the optical system, a reflection type illumination optical system which converges light rays emitted from a light source to irradiate the mask with the light rays, and a reflection type imaging optical system which converges and reflects some of scattering light rays from the mask to form an image on a detector are used.

11. A mask defect inspection apparatus comprising:
    an optical system configured to acquire a dark-field image by irradiating an exposure mask with light having a wavelength, the exposure mask containing a defect;
    a first image acquisition unit configured to acquire, using the optical system, an image of a partial region on the mask positioned at a defocus position spaced away from a just-in-focus position, such that an image of the partial region at the defocus position contains only a noise signal;
    a detection threshold decision unit configured to decide a detection threshold in a desired inspection region on the mask using signal intensities of the acquired image of the partial region and an area ratio between the desired inspection region and the partial region, so that a signal count indicating signal intensities not less than the detection threshold in the desired inspection region is not more than a target false detection count;

a second image acquisition unit configured to acquire, using the optical system, an image of the desired inspection region in a state in which the mask is positioned in a vicinity of the just-in-focus position; and a defect determination unit configured to determine a defect when a signal intensity of the acquired image of the desired inspection region indicates an intensity not less than the detection threshold.

12. The apparatus according to claim 11, wherein the mask is an extreme-ultraviolet ray exposure blank mask.

13. The apparatus according to claim 11, wherein the defocus position is set to be not less than five times of a value obtained by dividing the wavelength of the light by the square of the numerical aperture of the optical system.

14. The apparatus according to claim 11, wherein an average value of image intensities in a region outside a region having a position of interest as a center is calculated as a background, a sum total of values obtained by subtracting the background from image intensities of the region having the position of interest as the center is calculated, and the calculated sum total is used as the signal intensities of the image of the partial region or the desired inspection region.

15. The apparatus according to claim 11, wherein the optical system comprises a reflection type illumination optical system which converges light rays emitted from a light source to irradiate the mask with the light rays, and a reflection type imaging optical system which converges and reflects some of scattering light rays from the mask to form an image on a detector.

16. The apparatus according to claim 11, wherein the threshold decision unit calculates a first signal count distribution for a predetermined threshold by plotting signal counts indicating intensities not less than the predetermined threshold of signal intensities of the acquired image of the partial region, calculates a second signal count distribution in the desired inspection region by multiplying the first signal count distribution by an area ratio between the partial area and the desired inspection area, generates an approximate curve by fitting-approximating the second signal count distribution using an arbitrary function, calculates a signal intensity at which a signal count matches an arbitrary target false detection count in the generated approximate curve, and decides the signal intensity as the threshold.

* * * * *